United States Patent [19]

Denny et al.

[11] Patent Number: 4,894,210

[45] Date of Patent: Jan. 16, 1990

[54] PURIFICATION OF A HYDROCARBON MIXTURE

[75] Inventors: Patrick J. Denny, County Durham; Alan E. Thomas; Peter J. Carnell, both of Cleveland, all of England

[73] Assignee: Imperial Chemical Industries plc, London, England

[21] Appl. No.: 876,747

[22] Filed: Jun. 20, 1986

[30] Foreign Application Priority Data

Jul. 9, 1985 [GB] United Kingdom ............... 8517333

[51] Int. Cl.$^4$ ............................................. C01B 31/20
[52] U.S. Cl. ..................................... 423/230; 208/213; 585/802; 585/910; 585/911; 55/35; 55/73; 55/75; 423/249
[58] Field of Search .................... 423/230; 208/213; 585/802, 910, 911; 55/73, 35, 75

[56] References Cited

U.S. PATENT DOCUMENTS

| 2,037,790 | 4/1936 | Ipatieff | 208/213 |
|---|---|---|---|
| 2,259,409 | 10/1941 | Leuna et al. | 423/230 |
| 2,901,326 | 8/1959 | Kurata et al. | 423/230 |
| 2,951,032 | 8/1960 | Inwood | 208/213 |
| 3,223,746 | 12/1965 | Hammond et al. | 585/911 |
| 3,935,295 | 1/1976 | La Hue et al. | 423/230 |
| 4,088,736 | 6/1978 | Courty et al. | 423/230 |
| 4,097,544 | 6/1978 | Hengstebeck | 585/911 |
| 4,144,281 | 3/1979 | Chapman et al. | 585/911 |
| 4,287,377 | 9/1981 | Maslin et al. | 585/911 |
| 4,313,820 | 2/1982 | Farha, Jr. et al. | 208/213 |
| 4,358,297 | 11/1982 | Eberly, Jr. | 423/230 |
| 4,374,105 | 2/1983 | Anderson et al. | 423/230 |
| 4,399,112 | 8/1983 | Voirin | 423/230 |
| 4,442,078 | 4/1984 | Jalan et al. | 423/230 |
| 4,519,992 | 5/1985 | Alkhazov et al. | 423/231 |
| 4,533,529 | 8/1985 | Lee | 423/230 |
| 4,599,161 | 7/1986 | Scinta et al. | 423/230 |
| 4,608,240 | 8/1986 | Villarreal-Trevino et al. | 423/230 |
| 4,613,344 | 9/1986 | Henrich et al. | 423/230 |
| 4,673,557 | 6/1987 | Nieskeno et al. | 423/230 |

FOREIGN PATENT DOCUMENTS 0087834  5/1985  Japan ................................ 423/230

OTHER PUBLICATIONS

"Heat Blance", *Unit Processing and Principles of Chemical Engineering*, by John Olson, pp. 1–3, D. Van Nostrand Co. Inc., N.Y., 1932.

*Primary Examiner*—Helane Myers
*Attorney, Agent, or Firm*—Cushman, Darby & Cushman

[57] ABSTRACT

Desulphurization of saturated or near saturated gaseous hydrocarbon stream is effected using a bed of a particulate adsorbent comprising zinc oxide. Condensation of the higher boiling components is avoided by heating the raw gas to a temperature at least 10° C. above its dew point. This heating is effected by heat exchange with the heated desulphurized gas and by heat exchange with the combustion products of a minor part stream taken from the raw gas and/or from the desulphurized product gas stream. The absorbent particles preferably have a high BET surface area and pore volume.

4 Claims, 1 Drawing Sheet

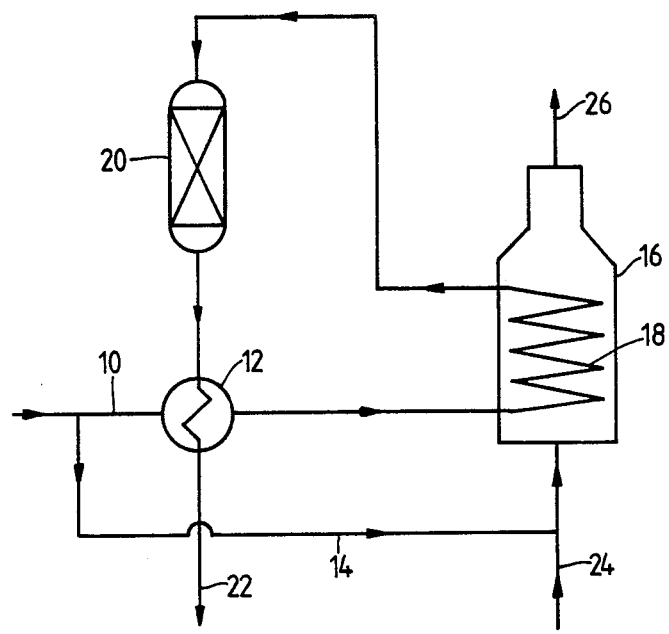

PURIFICATION OF A HYDROCARBON MIXTURE

This invention relates to hydrocarbon purification and in particular to the removal of sulphur compounds from a gaseous hydrocarbon stream.

As produced gaseous hydrocarbon streams generally contain small amounts of hydrogen sulphide and/or other sulphur compounds such as carbonyl sulphide. Before use it is generally desirable to reduce the sulphur compounds content of the gaseous hydrocarbon stream to a low level. Sulphur may be removed by contact of the gaseous hydrocarbon stream with a bed of a particulate absorbent material, such as zinc oxide.

Gaseous hydrocarbon streams obtained from wells in oil or gas fields generally contain methane in admixture with higher hydrocarbons and other compounds such as water and/or carbon dioxide and/or nitrogen. Often the gas obtained from the well is subjected to a preliminary compression and condensation step to separate higher boiling materials. After such compression and condensation the gas stream will typically be at a pressure of 10 to 200 bar abs and at a relatively low temperature, typically in the range $-10$ to $+10°$ C., and will be at, or near, saturation with such higher boiler materials. It is not practical to contact that gas stream at once with a solid absorbent for sulphur compounds, because condensation of such higher boiling components on the absorbent would be liable to take place at once or in the event of a fluctuation in the composition, pressure, or temperature of the gas stream. Such condensation is particularly liable to occur where the gas stream is under such conditions that it is close to its critical state: here the latent heat of condensation is less than 10% of its value at atmospheric pressure, so that the so-called "retrograde" condensation or evaporation is liable to occur. It is therefore desirable to heat the gas mixture to such a temperature that condensation of higher boiling materials is avoided. Such heating also enables the absorbent to be used at a temperature at which its absorption capacity is high.

In the present invention the heating is effected by combustion of a small part stream of the gas.

Accordingly the present invention provides a continuous process for the desulphurisation of a raw gas stream containing methane in admixture with at least one higher boiling component selected from water and one or more hydrocarbons of higher molecular weight than methane, said raw gas stream having such a composition and being at such temperature and pressure that the concentration of at least one of said higher boiling components is at least 90% of saturation comprising (a) heating an inlet gas stream consisting of said raw gas stream, or a major part thereof, to a temperature at least 10°, preferably at least 20° C., above the dew point of said raw gas stream, thereby producing a heated gas stream;
(b) contacting said heated gas stream with a bed of a particulate solid absorbent material comprising zinc oxide, thereby producing a desulphurised gas stream;
(c) heat exchanging the desulphurised gas stream with the inlet gas stram whereby to provide at least part of the heat required for step (a);
(d) providing the remainder of the heat required in step (a) by combusting a minor part gas stream consisting of
 (i) part of the desulphurised gas stream, or
 (ii) where the inlet gas stream is a major part of the raw gas stream, the remainder of the raw gas stream and, optionally, part of said desulphurised gas stream, and
heat exchanging the combustion products with said inlet gas stream, before or after step (c).

The raw gas stream typically contains hydrocarbons up to those containing six carbon atoms. Usually it will contain, in addition to methane, one or more of ethane, propane, propene, butanes, and butenes. While the invention is of particular importance where the raw gas is a "wet" natural gas or oilfield associated gas, the invention is also of utility with other raw gas streams, for example where the raw gas is the product of fractionating a gas mixture produced by cracking by hydrocracking a normally liquid hydrocarbon feedstock, or the gaseous byproduct of a zeolite-catalysed conversion of a feedstock such as methanol to gasoline.

The composition of the raw gas, where the latter is a natural or oilfield associated gas, expressed by volume, is typically

| | |
|---|---|
| ethane | 2 to 20% |
| propane plus propene | 1 to 10% |
| butanes plus butenes | 0.5 to 5% |
| higher hydrocarbons | 0.2 to 2% |
| carbon dioxide | 0 to 20% |
| nitrogen | 0 to 20% |
| water | up to saturation |
| methane | balance. |

The sulphur compounds initiaally present in the hydrocarbon stream usually include hydrogen sulphide and/or carbonyl sulphide, and possibly carbon disulphide, methyl mercaptan, diethyl sulphide, and/or tetrahydrothiophene. The total initial concentration of sulphur compounds, expressed as sulphur equivalent hydrogen sulphide, is typically in the range 10 to 1000 ppm by volume of the hydrocarbon stream. The absorption can be conducted so that a substantial proportion, e.g. over 75% by volume, of the sulphur content of the hydrocarbon stream can be removed. Typically the sulphur compounds content of the hydrocarbon stream leaving the absorbent bed is under 10, for example under 5, ppm by volume, expressed as above, but this is a matter of design, depending on the user's requirements.

In the process of the invention the temperature of the raw gas is, as mentioned above, typically in the range $-10°$ to $+10°$ C. The heating step is preferably conducted so as to increase the temperature to at least 40° C., and preferably to within the range 80° to 200° C. The temperature of the desulphurised product gas stream, after heat exchange with the inlet gas, is preferably above its dew point and is preferably at least 5° C. higher than the temperature of the raw gas. However the desulphurised product gas stream temperature is preferably below 25° C. Normally the heating of the inlet gas by heat exchange with the combustion products of the minor stream is effected after the heat exchange between the desulphurised gas stream and the inlet gas stream, so that the temperature difference in the latter heat exchange is maximised. The minor part stream that is combusted is typically in the range 0.02 to 2% by volume of the raw gas. The minor part stream may be part of the raw gas, i.e. before desulphurisation, and/or may be part of the desulphurised gas stream.

The minor part stream may be taken from the raw gas before, or after, heating of the latter. Where the minor part gas stream comprises desulphurised gas, likewise it may be taken from the desulphurised gas stream before, or after, heat exchange with the inlet gas.

The absorbent material preferably comprises at least 60, especially at least 80, % by weight of zinc of oxide, calculated the absorbent material non-volatile at 900° C. As used in the process the zinc oxide may be, at least initially, wholly or partly hydrated or in the form of a salt of a weak acid, e.g. a carbonate.

The absorbent material is preferably in the form of porous agglomerates, as may be made, for example, by mixing a finely divided zinc oxide composition with a cement binder and a little water, insufficient to give a slurry, and then granulated or extruded. In order to aid access of the heated gas stream into the particles, the latter may be provided in the form of extruded pellets having a plurality of through passages. Typically the BET surface area of the particles is at least 20, preferably preferably in the range 50 to 200, $m^2.g^{-1}$, and the pore volume of the particles is preferably at least 0.2 $cm^3.g^{-1}$.

Since the absorption efficiency and hence the life of a zinc oxide particulate bed depends on the rate of diffusion of the zinc sulphide formed by reaction of the zinc oxide with the sulphur compounds towards the interior of the particle, particularly at low absorption temperatures, it is preferably to employ zinc oxide particles having a high pore volume, above 0.2 $cm^3.g^{-1}$ and high surface area, above 50 $m^2.g^{-1}$. Thus while zinc oxide particles having a lower pore volume and a surface area of the order of 25 to 30 $m^2.g^{-1}$ can be employed, the bed life at low absorption temperatures is relatively low, necessitating the use of large bed volumes to avoid premature break-through of the sulphur compounds into the exit gas stream. By using a bed of particles of pore volume above, for example, 0.25 $cm^3.g^{-1}$ and surface area above, for example, 70 $m^2.g^{-1}$, the bed volume can be markedly reduced, e.g. to about one third of that required with particles of low pore volume and surface area 25 to 30 $m^2.g^{-1}$. The particles employed thus preferably have a surface area above 50, particularly above 70, $m^2.g^{-1}$ and a pore volume above 0.25 $cm^3.g^{-1}$.

Preferred absorbent materials for the process have a hydrogen sulphide absorption capacity of at least 20, especially at least 25, % of the theoretical, at a temperature of 25° C., as determined in a standard test in which a mixture of hydrogen sulphide (2000 ppm by volume), carbon dioxide (4% by volume), and methane (balance) is passed through a bed of the particles at atmospheric pressure and a space velocity of 700 $h^{-1}$ using a bed of circular cross section having a length to diameter ratio of 5.

A particularly suitable particulate zinc oxide material is that sold by Imperial Chemical Industries plc as "Catalyst 75-1". These particles are granules typically having a surface area of the order of 80 $m^2.g^{-1}$ and a pore volume of about 0.3 $cm^3.g^{-1}$, and an adsorption capacity of about 27% of theoretical when measured by the above procedure.

The particulate bed can be in the form of a fixed bed, a liftable bed, or a fluidised bed.

The process can be the sole sulphur removal step applied to the raw gas stream or can be used in combination with one or more of the following:

upstream distillative removal of hydrogen sulphide;

upstream removal of sulphur compounds and/or carbon dioxide in an absorbent liquid such as an ethanolamine, "Sulpholane", or methanol;

upstream hydrogenative conversion of organic sulphur compounds to hydrogen sulphide;

downstream removal of carbonyl sulphide, carbon disulphide, methyl mercaptan and/or residual hydrogen sulphide by reaction with caustic alkali or sodalime, possibly in the presence of an alcohol.

One preferred form of the invention is shown as a flowsheet in the accompanying drawing.

"Wet" oilfield associated gas is divided into a major part stream which is fed via line 10 to a heat exchanger 12, and a minor part stream which is fed via line 14 to a furnace 16. The major part stream is heated in heat exchanger 12 to a level substantially above its dew point and then heated further in pipe coils 18 disposed in furnace 16. The resultant heated gas is then passed through a bed of particulate zinc oxide in a reactor 20 wherein sulphur compounds are absorbed so that the gas stream is substantially freed of the sulphur compounds. The resultant desulphurised gas is then cooled in heat exchanger 12, thereby heating the incoming "wet" gas stream, and is then discharged via line 22 to users. The minor part stream is mixed with air supplied via line 24 prior to, or as, it enters the burner of furnace 16. Hot gas resulting from the combustion of the minor part stream is passed over the pipe coils 18 to heat them and then is discharged to the atmosphere via flue 26. The rate of flow of the minor part stream is very small as a result of the heat recovery effected in heat exchanger 12, but suffices to make up for the heat losses and to ensure a final outlet temperature, i.e. in line 22, sufficient to avoid condensation of higher hydrocarbons and water. At the same time, the temperature at which the gas contacts the zinc oxide is high enough to ensure a high capacity of the absorbent bed for sulphur compounds.

If it is objectionable to discharge an effluent containing sulphur dioxide, which results from the combustion of the sulphur compounds in the minor part stream, the gas to the burner of furnace 16 can be taken from a point downstream of reactor 20 instead of from the raw inlet gas.

In a calculated example the conditions as as follows:

| Starting gas | |
|---|---|
| Flow rate | 24800 kg mol. $h^{-1}$ |
| Temperature | 4° C. |
| Pressure | 95 bar abs. |
| Composition | |
| Methane | 79.898% v/v |
| Ethane | 10.211% v/v |
| Propane | 5.601% v/v |
| Butane | 2.270% v/v |
| Carbon dioxide | 1.270% v/v |
| Nitrogen | 0.750% v/v |
| Hydrogen sulphide | 10 ppm v/v |

Three cases are considered, differing in the temperature at which the desulphurised product gas stream is delivered via line 22:

| | | | |
|---|---|---|---|
| Line 22 delivery temperature °C. | 20 | 15 | 10 |
| Heat exchanger 12 outlet temperature °C. (heated gas) | 126.5 | 135.0 | 141.6 |
| Reactor 20 inlet temperature °C. | 150 | 150 | 150 |
| Minor part stream flow rate | 36.9 | 23.5 | 13.2 |

| -continued | | | |
|---|---|---|---|
| kg mol. h$^{-1}$ | | | |
| Heat exchanger 12 heat load MW | 50.9 | 54.1 | 56.6 |
| Furnace 16 heat load MW | 9.0 | 5.8 | 3.2 |
| Log mean ΔT across heat exchanger 12° C. | 19.5 | 12.9 | 7.1 |

(log mean ΔT is defined as the quotient of the hot end temperature approach less the cold end temperature approach divided by the natural logarithm of the ratio of the hot end temperature approach to the cold end temperature approach).

If reactor 20 has a volume providing for a bed of 100 m$^3$ of "ICI Catalyst 75-1" in the form of granules having a diameter in the range 0.5 to 5 mm, it is to be expected that operation for one year will be possible before the outlet hydrogen sulphide content exceeds 0.5 ppm by volume.

We claim:

1. A continuous process for the desulphurisation of a raw gas stream containing methane in admixture with at least one higher boiling component selected from water and one or more hydrocarbons of higher molecular weight than methane, said raw gas stream having such a composition and being at such a temperature, in the range of −10° to +10° C., and pressure, in the range 10 to 200 bar abs., that the concentration of at least one of said higher boiling components is at least 90% of the concentration of said higher boiling component at which said raw gas stream would be saturated with said higher boiling component, comprising:

(a) heating an inlet gas stream consisting of said raw gas stream, or a major part thereof, to a temperature that is at least 10° C. above the dew point of said raw gas stream and is in the range 80° to 200° C. thereby producing a heated gas stream;

(b) contacting said heated gas stream with a bed of a particulate solid absorbent material comprising zinc oxide, thereby producing a desulphurised gas stream; and (c) combusting a gas stream consisting of:
   (i) part of the desulphurised gas stream, or
   (ii) where said inlet gas stream is a major part of the raw gas stream, the remainder of the raw gas stream, or
   (iii) a combination of (i) and (ii) thereby providing a heated combustion products stream; said heating step (a) being effected by:

heat exchanging the inlet gas stream with the desulphurised gas steam, thereby forming a partly heated inlet stream and a cooled desulphurised gas stream that has a temperature below 25° C. and that is at least 5° above the temperature of said raw gas stream; and further heating said partly heated inlet stream by heat exchanging the partly heated gas stream with the heated combustion products stream.

2. A process according to claim 1 wherein the raw gas is natural or oilfield associated gas.

3. A process according to claim 1 wherein that gas stream which is to be combusted so as to provide said heated combustion products stream, is equivalent in volume to 0.02 to 0.2% by volume of the raw gas.

4. A process according to claim 1 wherein the absorbent material has a BET surface area in the range 50 to 200 m$^2$.g$^{-1}$ and a pore volume of at least 0.2 cm$^3$.g$^{-1}$.

* * * * *